(12) United States Patent
Honda

(10) Patent No.: US 6,958,042 B2
(45) Date of Patent: *Oct. 25, 2005

(54) ULTRASONIC TRANSMISSION/RECEPTION METHOD, ULTRASONIC TRANSMISSION/RECEPTION APPARATUS, ULTRASONIC IMAGING METHOD AND ULTRASONIC IMAGING APPARATUS

(75) Inventor: Masayoshi Honda, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 212 days.

This patent is subject to a terminal disclaimer.

(21) Appl. No.: 10/119,252

(22) Filed: Apr. 9, 2002

(65) Prior Publication Data

US 2002/0151798 A1 Oct. 17, 2002

(30) Foreign Application Priority Data

Apr. 11, 2001 (JP) ............................. 2001-112466

(51) Int. Cl.[7] .............................................. A61B 8/06
(52) U.S. Cl. .................................................... 600/458
(58) Field of Search ............................... 600/443, 447, 600/455–456, 453, 437, 458–9; 125/916; 73/615–626

(56) References Cited

U.S. PATENT DOCUMENTS

| 5,526,816 A | 6/1996 | Arditi |
| 5,560,364 A | 10/1996 | Porter |
| 5,567,415 A | 10/1996 | Porter |
| 5,701,897 A | 12/1997 | Sano |
| 5,820,561 A | 10/1998 | Olstad et al. |
| 5,833,615 A * | 11/1998 | Wu et al. .................... 600/458 |
| 5,846,200 A | 12/1998 | Schwartz |
| 5,865,751 A | 2/1999 | Okumo et al. |
| 5,873,829 A | 2/1999 | Kamiyama et al. |
| 5,935,074 A | 8/1999 | Mo et al. |
| 5,947,904 A * | 9/1999 | Hossack et al. ............ 600/458 |
| 6,010,456 A * | 1/2000 | Rhyne ......................... 600/447 |
| 6,174,286 B1 | 1/2001 | Ramamurthy et al. |
| 6,213,947 B1 * | 4/2001 | Phillips ....................... 600/443 |
| 6,238,426 B1 | 5/2001 | Chen |
| 6,241,674 B1 * | 6/2001 | Phillips et al. .............. 600/443 |
| 6,312,384 B1 * | 11/2001 | Chiao .......................... 600/443 |
| 6,322,510 B1 | 11/2001 | Kataoka et al. |
| 6,340,348 B1 * | 1/2002 | Krishnan et al. ........... 600/447 |
| 6,364,835 B1 | 4/2002 | Hossack et al. |
| 6,375,618 B1 * | 4/2002 | Chiao et al. ................ 600/447 |
| 6,491,631 B2 * | 12/2002 | Chiao et al. ................ 600/443 |
| 6,558,328 B2 * | 5/2003 | Chiao et al. ................ 600/447 |

* cited by examiner

Primary Examiner—Francis J. Jaworski
(74) Attorney, Agent, or Firm—Carl B. Horton, Esq.; Armstrong Teasdale LLP

(57) ABSTRACT

In order to capture an ultrasonic image of high quality using ultrasound having a low sound pressure that does not break a contrast agent, scanning is performed during a pause period of intermittent scanning, using ultrasound that has a sound pressure insufficient to break the contrast agent and has undergone predetermined modulation; pulse compression is performed on an echo received signal; and an image is produced based on the pulse-compressed echo received signal.

16 Claims, 14 Drawing Sheets

FIG. 8
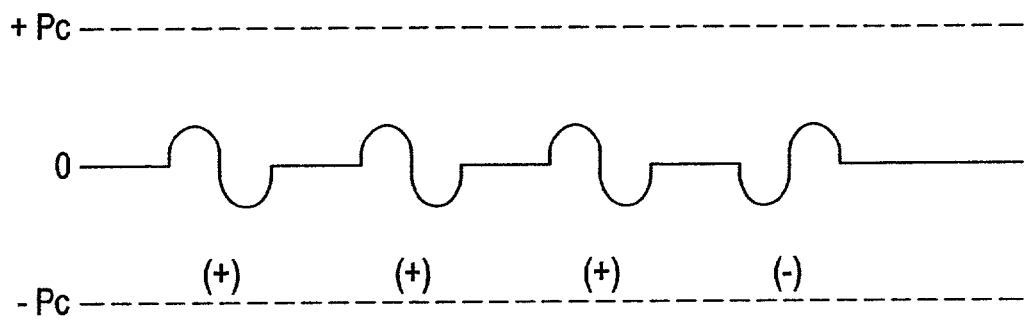
FIG. 9
| Code Length | Code Sequence |
|---|---|
| N=2 | + + or + - |
| N=3 | + + - |
| N=4 | + + - + or + + + - |
| N=5 | + + + - + |
| N=7 | + + + - - + - |
| N=11 | + + + - - - + - - + - |
| N=13 | + + + + + - - + + - + - + |
FIG. 10
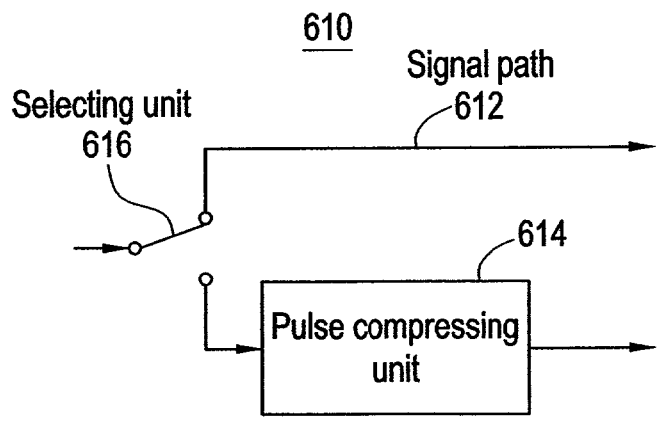

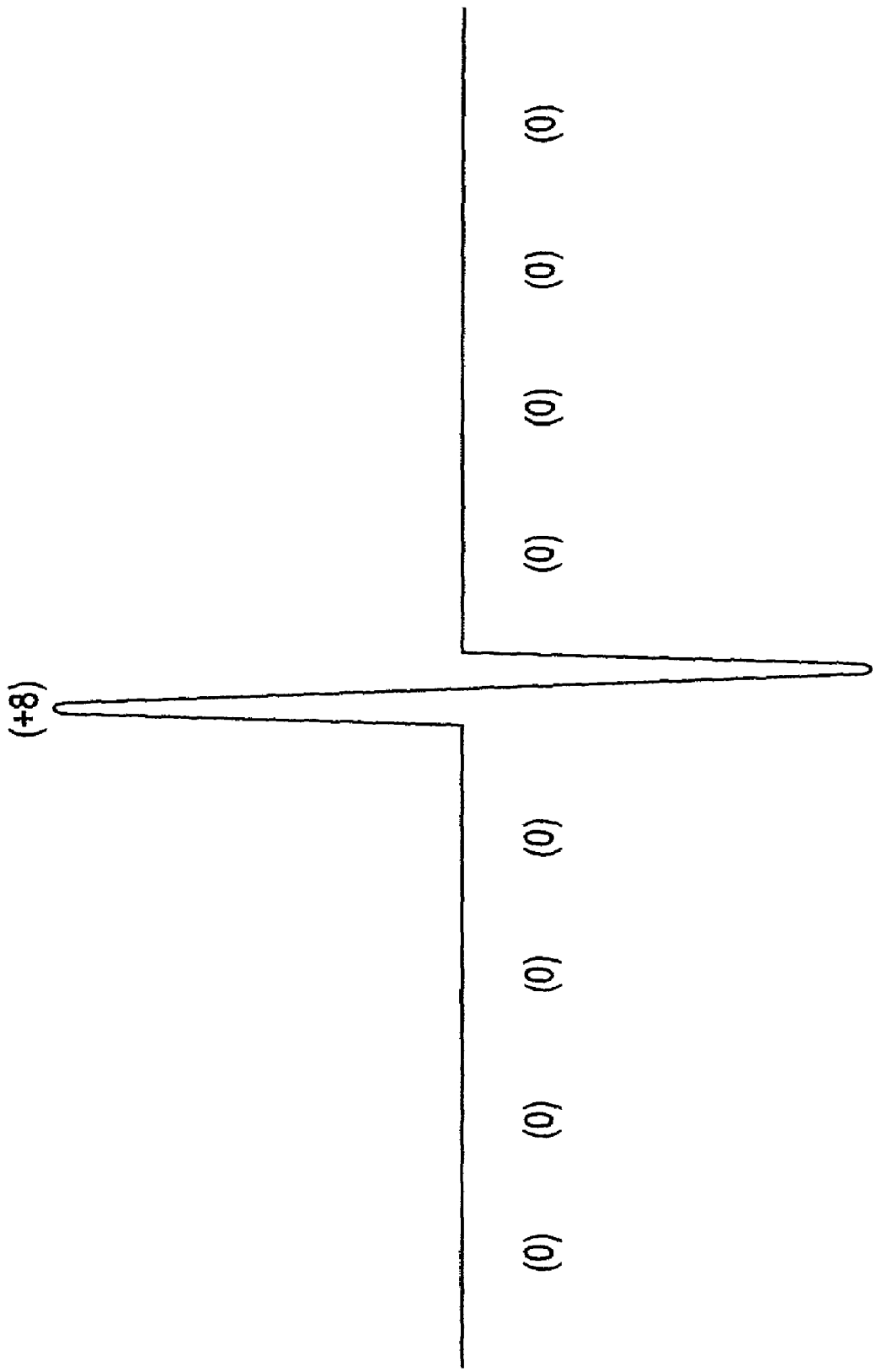

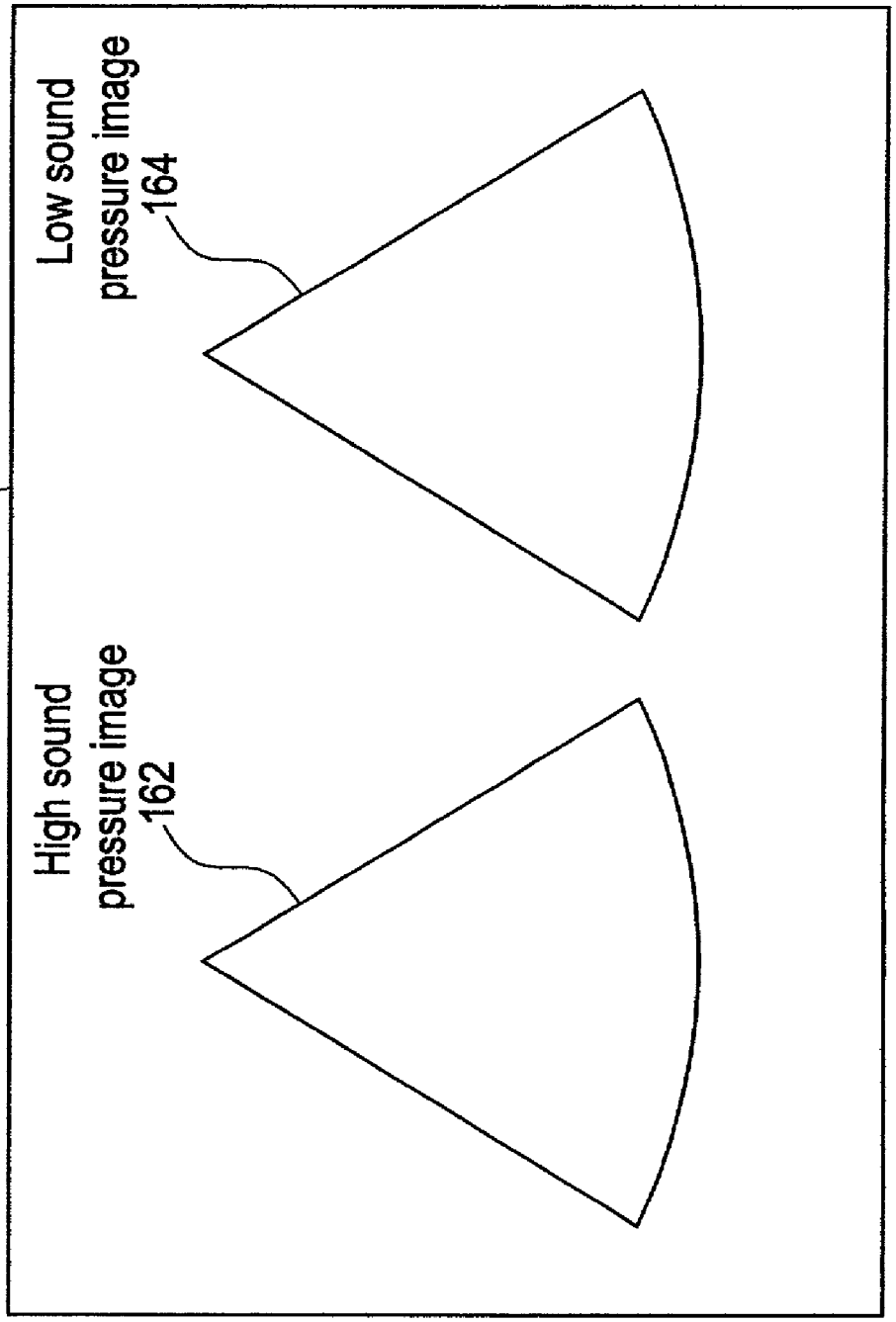

ULTRASONIC TRANSMISSION/RECEPTION METHOD, ULTRASONIC TRANSMISSION/RECEPTION APPARATUS, ULTRASONIC IMAGING METHOD AND ULTRASONIC IMAGING APPARATUS

CROSS REFERENCE TO RELATED APPLICATIONS

This application claims the benefit of Japanese Application No. 2001-112466 filed Apr. 11, 2001.

BACKGROUND OF THE INVENTION

The present invention relates to an ultrasonic transmission/reception method, ultrasonic transmission/reception apparatus, ultrasonic imaging method and ultrasonic imaging apparatus, and particularly to an ultrasonic transmission/reception method, ultrasonic transmission/reception apparatus, ultrasonic imaging method and ultrasonic imaging apparatus for imaging an object into which an ultrasonic contrast agent is injected.

In ultrasonic imaging, an echo of ultrasound transmitted into an object is used to capture a tomographic image, and the image is displayed as a B-mode image. Moreover, a Doppler shift of the ultrasonic echo is used to capture a dynamic image of blood flow etc., and the image is displayed as a color Doppler image.

When the signal intensity of the echo needs to be increased, a region of interest (ROI) is infused with a contrast agent using the blood flow. The contrast agent is a collection of microscopic bubbles having a diameter of several micrometers.

Such a contrast agent is broken up and disappears when exposed to ultrasound having a sound pressure greater than a certain level and will generate no echo next time. Therefore, the next imaging is performed after the contrast agent has again reached the site being imaged.

For this reason, the ultrasonic imaging using the contrast agent performs intermittent image capture (scanning) with a pause period of, for example, from several seconds to several tens of seconds after every imaging. Each tomographic image obtained from the scanning is displayed as a freeze image and is updated every time the next scanning image is obtained.

In order to make it possible to observe the state of the imaged site in real time during the pause period, the same region is imaged using ultrasound having a sound pressure reduced to a degree such that it does not break the contrast agent.

However, the image captured using the ultrasound having a sound pressure reduced to a degree such that the it does not break the contrast agent has poor quality because of the low SNR (signal-to-noise ratio) of the echo received signal.

SUMMARY OF THE INVENTION

It is therefore an object of the present invention is to provide an ultrasonic transmission/reception method, ultrasonic transmission/reception apparatus, ultrasonic imaging method and ultrasonic imaging apparatus that enable an image to be obtained with high quality using ultrasound having a sound pressure reduced to a degree such that it does not break a contrast agent.

(1) The present invention, in one aspect thereof for solving the aforementioned problem, is an ultrasonic transmission/reception method, comprising the steps of: intermittently scanning an imaged region with a predetermined pause period using ultrasound that has a sound pressure sufficient to break a contrast agent, and receiving an echo of the ultrasound; continuously scanning the same region as the imaged region during the pause period using ultrasound that has a sound pressure insufficient to break the contrast agent and has undergone predetermined modulation, and receiving an echo of the ultrasound; and performing pulse compression on an echo received signal obtained by the continuous scanning.

(2) The present invention, in another aspect thereof for solving the aforementioned problem, is an ultrasonic transmission/reception apparatus, comprising: first ultrasound transmitting/receiving means for scanning an imaged region using ultrasound that has a sound pressure sufficient to break a contrast agent, and receiving an echo of the ultrasound; second ultrasound transmitting/receiving means for scanning the same region as the imaged region using ultrasound that has a sound pressure insufficient to break the contrast agent and has undergone predetermined modulation, and receiving an echo of the ultrasound; pulse compressing means for performing pulse compression on an echo received signal from the second ultrasound transmitting/receiving means; and control means for causing the first ultrasound transmitting/receiving means to intermittently perform the scanning with a predetermined pause period, and causing the second ultrasound transmitting/receiving means to continuously perform the scanning during the pause period.

(3) The present invention, in still another aspect thereof for solving the aforementioned problem, is an ultrasonic imaging method, comprising the steps of: intermittently scanning an imaged region with a predetermined pause period using ultrasound that has a sound pressure sufficient to break a contrast agent, and receiving an echo of the ultrasound; continuously scanning the same region as the imaged region during the pause period using ultrasound that has a sound pressure insufficient to break the contrast agent and has undergone predetermined modulation, and receiving an echo of the ultrasound; performing pulse compression on an echo received signal obtained by the continuous scanning; and producing respective images based on an echo received signal obtained by the intermittent scanning and on an echo received signal after the pulse compression.

(4) The present invention, in still another aspect thereof for solving the aforementioned problem, is an ultrasonic imaging apparatus, comprising: first ultrasound transmitting/receiving means for scanning an imaged region using ultrasound that has a sound pressure sufficient to break a contrast agent, and receiving an echo of the ultrasound; second ultrasound transmitting/receiving means for scanning the same region as the imaged region using ultrasound that has a sound pressure insufficient to break the contrast agent and has undergone predetermined modulation, and receiving an echo of the ultrasound; pulse compressing means for performing pulse compression on an echo received signal from the second ultrasound transmitting/receiving means; control means for causing the first ultrasound transmitting/receiving means to intermittently perform the scanning with a predetermined pause period, and causing the second ultrasound transmitting/receiving means to continuously perform the scanning during the pause period; and image producing means for producing respective images based on an echo received signal from the first ultrasound transmitting/receiving means and on an echo received signal after the pulse compression from the second ultrasound transmitting/receiving means.

According to the invention of the aspects as described in (1) and (2), during the pause period, scanning is performed using ultrasound that has a sound pressure insufficient to break the contrast agent and has undergone predetermined modulation, an echo of the ultrasound is received, and the echo received signal is subjected to pulse compression; and therefore, an echo received signal can be obtained with a good SNR even if the transmitted ultrasound has a low sound pressure.

According to the invention of the aspects as described in (3) and (4), during the pause period, scanning is performed using ultrasound that has a sound pressure insufficient to break the contrast agent and has undergone predetermined modulation, and the echo received signal is subjected to pulse compression; and therefore, an echo received signal can be obtained with a good SNR even if the transmitted ultrasound has a low sound pressure. Moreover, since an image is produced based on such an echo received signal, an image of good quality can be obtained.

Preferably, the modulation is code modulation, in that the modulation of the transmitted ultrasound and the pulse compression of the echo received signal can be effectively performed.

Preferably, a code sequence for the code modulation is a Barker code, in that such a code has been well-established in practical applications such as radar technology.

Preferably, a code sequence for the code modulation is a Golay code, in that such a code has been well-established in practical applications such as radar technology, and it generates no side lobe.

Preferably, the modulation is linear frequency modulation, in that the modulation of the transmitted ultrasound and the pulse compression of the echo received signal can be easily achieved.

As described above in detail, the present invention can provide an ultrasonic transmission/reception method, ultrasonic transmission/reception apparatus, ultrasonic imaging method and ultrasonic imaging apparatus that enable an image to be obtained with high quality using ultrasound having a sound pressure reduced to a degree such that the ultrasound does not break a contrast agent.

Further objects and advantages of the present invention will be apparent from the following description of the preferred embodiments of the invention as illustrated in the accompanying drawings.

BRIEF DESCRIPTION OF THE DRAWINGS

FIG. 8 is a waveform diagram of transmitted ultrasound based on an output signal from a modulated signal generating unit.

FIG. 9 illustrates several code sequences of a Barker code.

FIG. 10 is a block diagram of part of the transceiver section.

FIGS. 14–16 illustrates pulse compression by the pulse compressing unit.

FIG. 18 is a schematic diagram showing an example of a screen displayed on a display section.

DETAILED DESCRIPTION OF THE INVENTION

Figure 1:
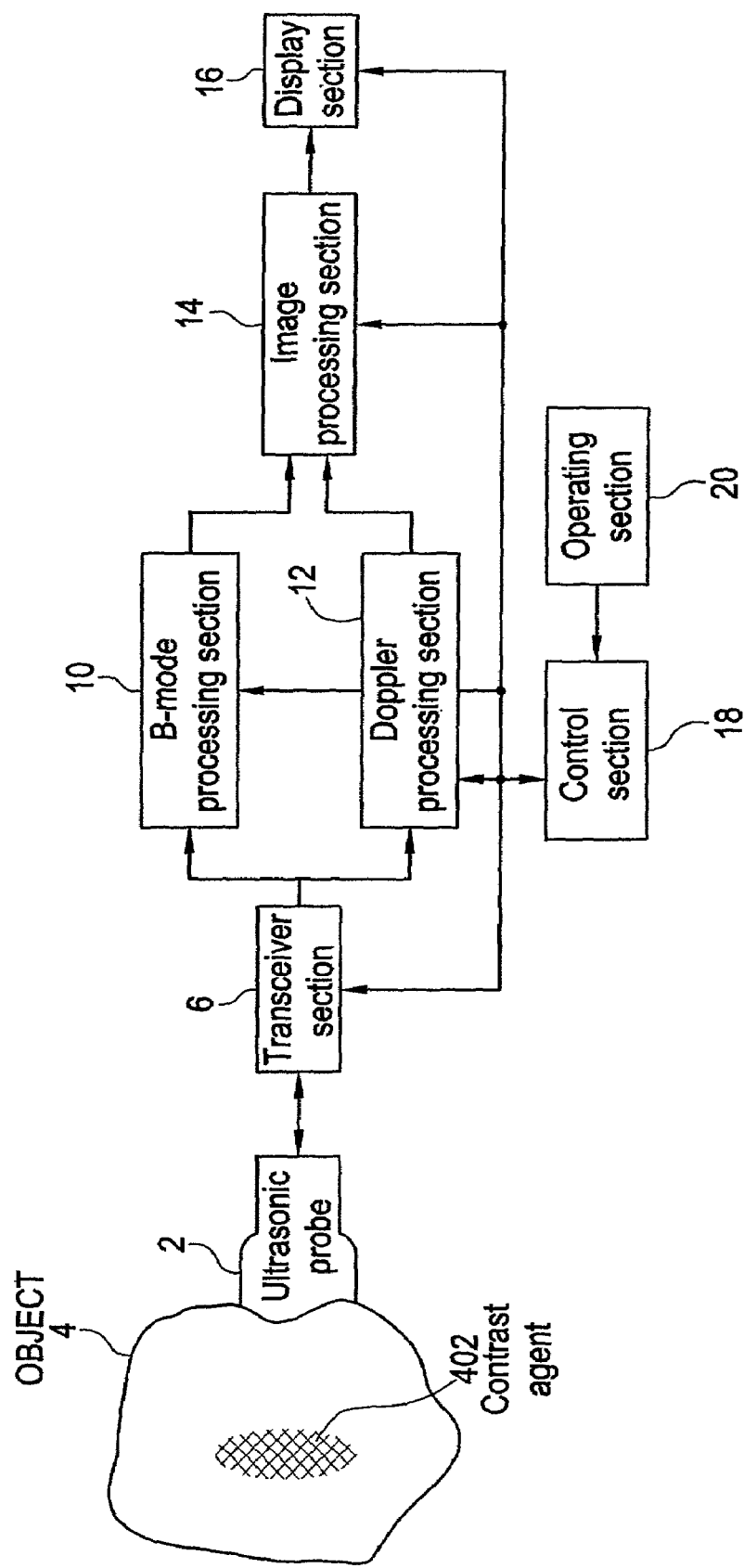
FIG. 1 is a block diagram of an apparatus in accordance with one embodiment of the present invention.

Several embodiments of the present invention will now be described in detail with reference to the accompanying drawings. It should be noted that the present invention is not limited to the embodiments. FIG. 1 shows a block diagram of an ultrasonic imaging apparatus, which is an embodiment of the present invention. The configuration of the apparatus represents an embodiment of the apparatus in accordance with the present invention. The operation of the apparatus represents an embodiment of the method in accordance with the present invention.

As shown in FIG. 1, the present apparatus has an ultrasonic probe 2. The ultrasonic probe 2 has an array of ultrasonic transducers (not shown). The individual ultrasonic transducers are made from a piezoelectric material such as PZT (lead zirconate titanate [Pb—Zr—Ti]) ceramic. The ultrasonic probe 2 is used abutted against an object 4 by a user. A region of interest in the object 4 is supplied with a contrast agent 402 using blood flow.

The ultrasonic probe 2 is connected to a transceiver section 6. The transceiver section 6 supplies driving signals to the ultrasonic probe 2 to transmit ultrasound. The transceiver section 6 also receives echo signals caught by the ultrasonic probe 2.

Figure 2:
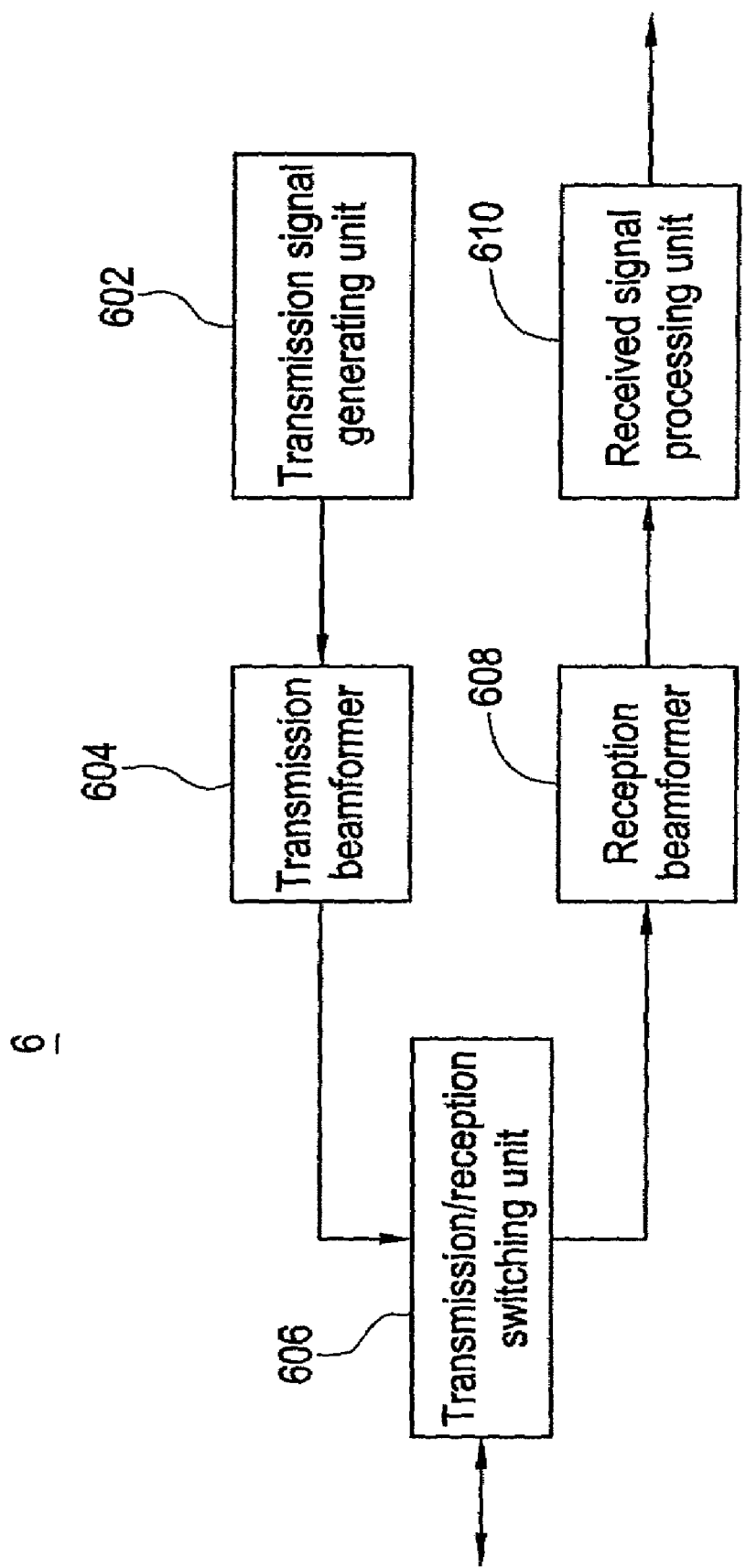
FIG. 2 is a block diagram of a transceiver section.

FIG. 2 shows a block diagram of the transceiver section 6. As shown, the transceiver section 6 has a transmission signal generating unit 602. The transmission signal generating unit 602 periodically generates a transmission signal, and inputs the signal to a transmission beamformer 604. The transmission signal generating unit 602 is controlled by a control section 18, which will be described later.

The transmission beamformer 604 is for performing beamforming for the transmission, involving generating a beamforming signal for forming an ultrasonic beam in a certain direction based on the transmission signal. The beamforming signal consists of a plurality of driving signals that are given respective time differences corresponding to the direction. The beamforming is controlled by the control section 18, which will be described later. The transmission beamformer 604 inputs the transmission beamforming signal to a transmission/reception switching unit 606.

The transmission/reception switching unit 606 inputs the beamforming signal to the ultrasonic transducer array. A plurality of ultrasonic transducers that constitute a transmission aperture in the ultrasonic transducer array generate ultrasound having respective phase differences corresponding to the time differences in the driving signals. By wavefront synthesis of the ultrasound, an ultrasonic beam is formed along an acoustic line in a certain direction.

The transmission/reception switching unit 606 is connected with a reception beamformer 608. The transmission/reception switching unit 606 inputs the echo signals caught by a reception aperture in the ultrasonic transducer array to the reception beamformer 608. The reception beamformer 608 is for performing beamforming for the reception corresponding to an acoustic line for the transmission, involving imparting time differences to a plurality of received echoes to adjust their phases, and then adding the echoes to form an echo received signal along an acoustic line in a certain direction. The reception beamforming is controlled by the control section 18, which will be described later.

The transmission of the ultrasonic beam is repeated at predefined time intervals according to the transmission signal generated by the transmission signal generating unit 602. Synchronously with the signal, the transmission beamformer 604 and the reception beamformer 608 change the direction of the acoustic line by a predefined amount. Thus, the interior of the object 4 is sequentially scanned by the acoustic line. The transceiver section 6 having such a configuration performs scanning as exemplarily shown in FIG. 3. Specifically, a fan-shaped two-dimensional region 206 is scanned in the θ-direction by an acoustic line 202 extending from an emission point 200 in the z-direction, and so-called sector scanning is carried out.

Figure 4:
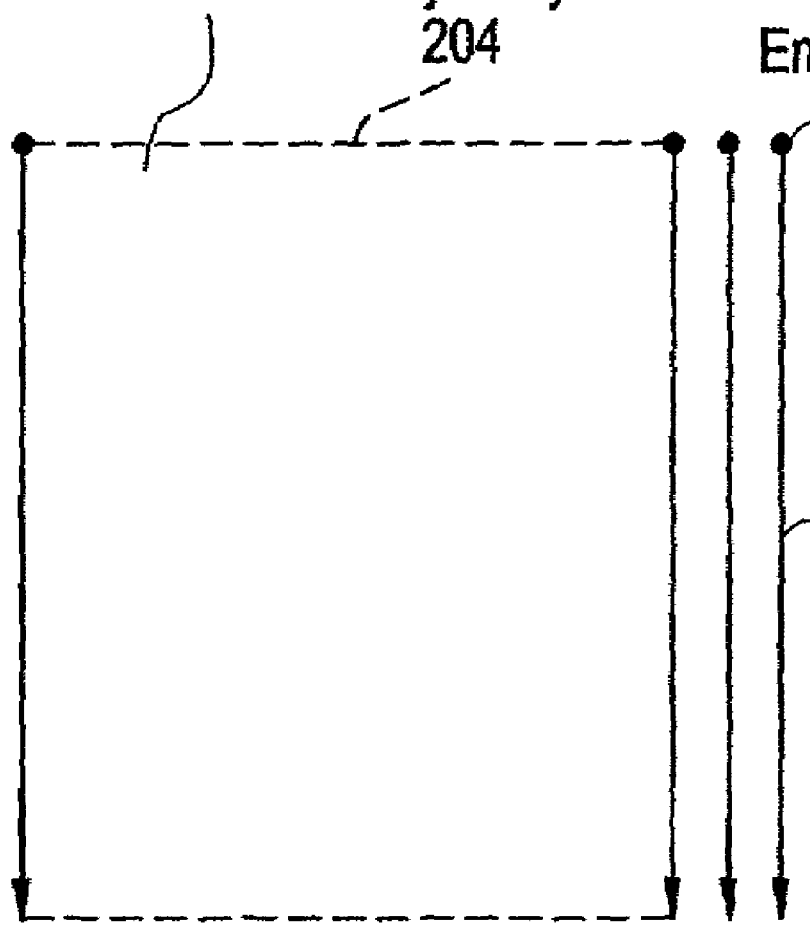

When the transmission and reception apertures are formed using part of the ultrasonic transducer array, scanning as exemplarily shown in FIG. 4 can be performed by sequentially shifting the apertures along the array. Specifically, a rectangular two-dimensional region 206 is scanned in the x-direction by translating an acoustic line 202, which emanates from an emission point 200 in the z-direction, along a linear trajectory 204, and so-called linear scanning is carried out.

Figure 5:
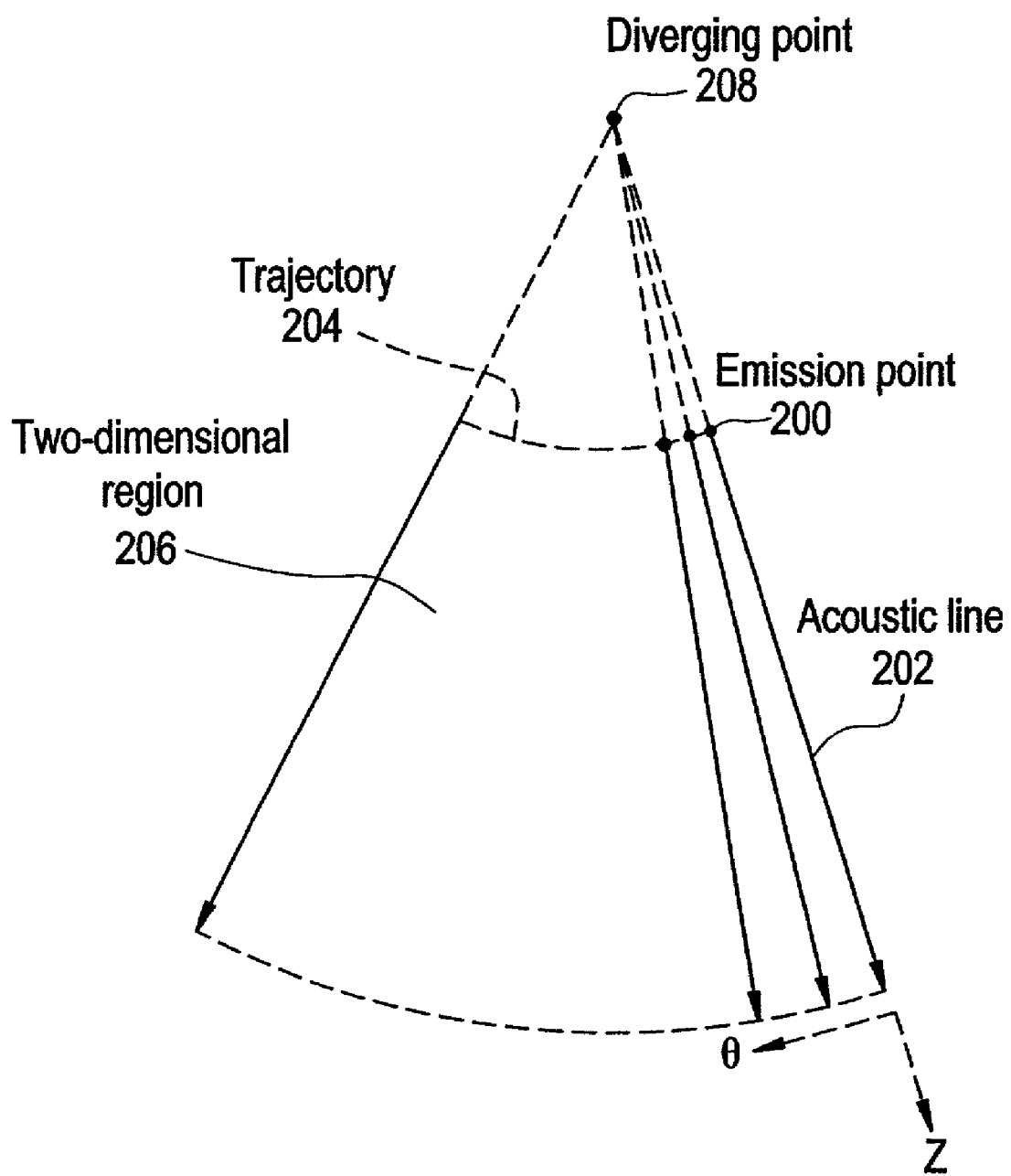

It will be easily recognized that when the ultrasonic transducer array is a so-called convex array, which is formed along an arc protruding in the direction of ultrasound transmission, a partial fan-shaped two-dimensional region 206 can be scanned in the θ-direction by performing acoustic line scanning similar to that of the linear scanning and moving an emission point 200 of an acoustic line 202 along an arc-like trajectory 204, as exemplarily shown in FIG. 5, and so-called convex scanning can thus be carried out.

The reception beamformer 608 is connected with a received signal processing unit 610. The received signal processing unit 610 performs processing as described later on an output signal, or an echo received signal, from the reception beamformer 608.

Under the control of the control section 18, which will be described later, scanning as described above is performed using two kinds of ultrasound having different sound pressures. One of the two kinds of ultrasound has a sound pressure sufficient to break the contrast agent, and the other has a sound pressure insufficient to break the contrast agent.

The scanning using the ultrasound having the higher sound pressure is intermittently performed. The interval between scannings, or the pause period, of the intermittent scanning ranges from several seconds to several tens of seconds. The scanning using the ultrasound having the lower sound pressure is continuously performed during the pause period of the intermittent scanning.

Figure 6:
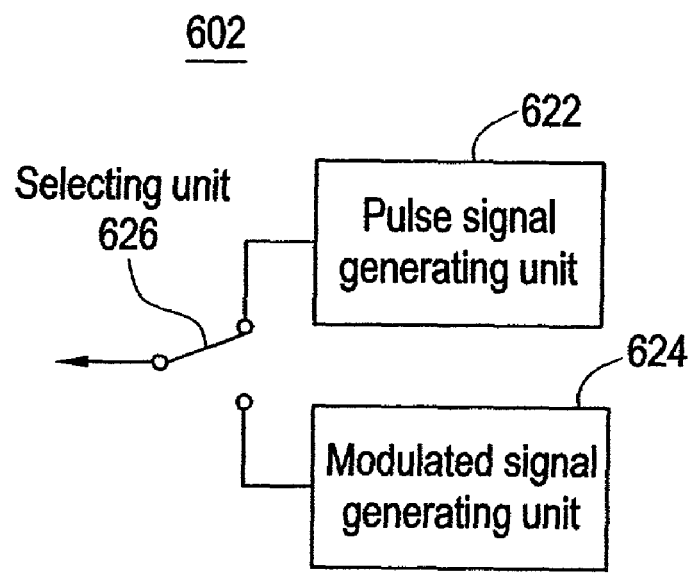
FIG. 6 is a block diagram of part of the transceiver section.

To perform the scanning using the two kinds of ultrasound, the transmission signal generating unit 602 has two signal generating units, as shown in FIG. 6. One of the two signal generating units is a pulse signal generating unit 622, and the other is a modulated signal generating unit 624. One of the output signals from these signal generating units is selected by a selecting unit 626 and input to the transmission beamformer 604. The selecting unit 626 is controlled by the control section 18, which will be described later.

Figure 7:
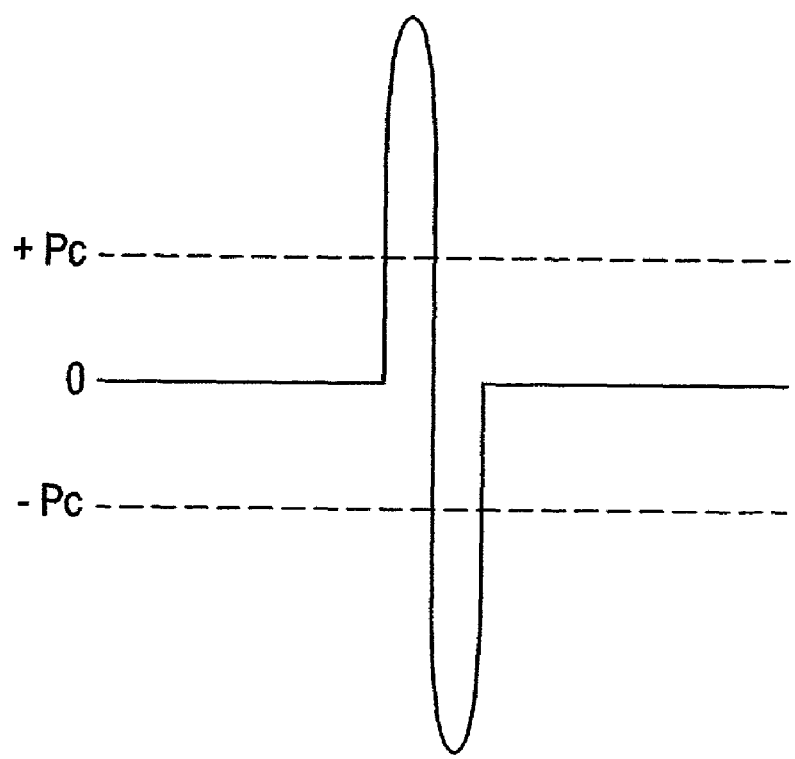
FIG. 7 is a waveform diagram of transmitted ultrasound based on an output signal from a pulse signal generating unit.

The output signal from the pulse signal generating unit 622 is a signal for causing the ultrasonic transducers to generate ultrasound having a sound pressure greater than a contrast agent breaking sound pressure Pc, as exemplarily shown in FIG. 7.

The output signal from the modulated signal generating unit 624 is a signal for causing the ultrasonic transducers to generate ultrasound having a sound pressure not greater than the contrast agent breaking sound pressure Pc, as exemplarily shown in FIG. 8.

As shown in FIG. 8, the output signal from the modulated signal generating unit 624 is modulated. Among other modulation schemes, a code modulation scheme, for example, is employed. As a code sequence for the modulation, there is employed, for example, a Barker code or a Golay code, both of which are practically used in pulse compression radar applications.

In FIG. 8, a case is illustrated in which the signal is modulated using the Barker code having a code length of four and a code sequence of [+++−]. The Barker code includes seven code sequences, as shown in FIG. 9. The code modulation may be achieved by any one of these code sequences.

To process the two kinds of echo received signals corresponding to the two kinds of transmitted ultrasound, the received signal processing unit 610 has a configuration as shown in FIG. 10. Specifically, as shown, an echo received signal is supplied to one of a through signal path 612 and a pulse compressing unit 614 according to selection by a selecting unit 616. The selecting unit 616 is controlled by the control section 18, which will be described later.

The selecting unit 616 is linked with the selecting unit 626. When the selecting unit 626 selects the pulse generating unit 622, the selecting unit 616 selects the through signal path 612; and when the selecting unit 626 selects the modulated signal generating unit 624, the selecting unit 616 selects the pulse compressing unit 614.

Thus, the echo received signal of ultrasound transmitted based on the output signal from the pulse generating unit 622 is input to the signal path 612; and the echo received signal of ultrasound transmitted based on the output signal from the modulated signal generating unit 624 is input to the pulse compressing unit 614.

The pulse compressing unit 614 performs pulse compression processing on the echo received signal. The pulse compression on the echo received signal of the code-modulated ultrasound is achieved by an autocorrelation calculation.

Figure 11:
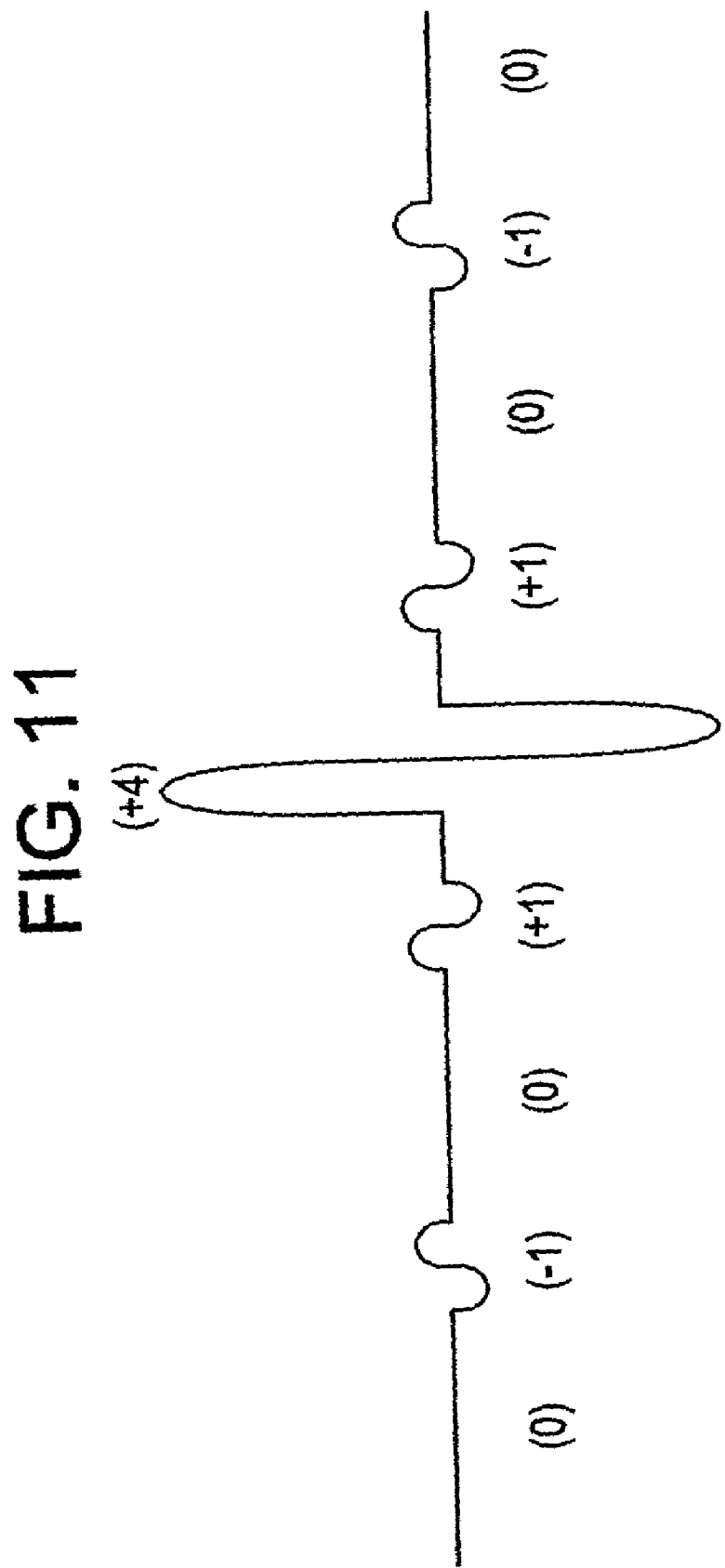
FIG. 11 illustrates pulse compression by a pulse compressing unit.

By performing the autocorrelation calculation on the echo received signal of the ultrasound modulated as described above, a pulse-compressed signal as shown in FIG. 11 is obtained. As shown, the pulse-compressed signal has a relative amplitude of 0, −1, 0, +1, +4, +1, 0, −1, 0 along a time axis.

By such pulse compression, a compressed pulse having a relative amplitude of 4 at the signal center can be obtained. In other words, a signal can be obtained that corresponds to an echo of transmitted ultrasound having a sound pressure four times that of the actually transmitted ultrasound.

Therefore, even if the sound pressure of the transmitted signal is low to the extent of being not greater than the contrast agent breaking sound pressure, an echo received signal having a good SNR can be obtained that is comparable with that in the case of the transmitted ultrasound having a sound pressure greater than the contrast agent breaking sound pressure.

The case in which the Golay code is employed is as follows: The Golay code has a pair of two code sequences

[+++−] and [++−+]. By using the code sequence pair, two series of transmitted ultrasound are obtained as shown in FIGS. 12 and 13.

Figure 12:
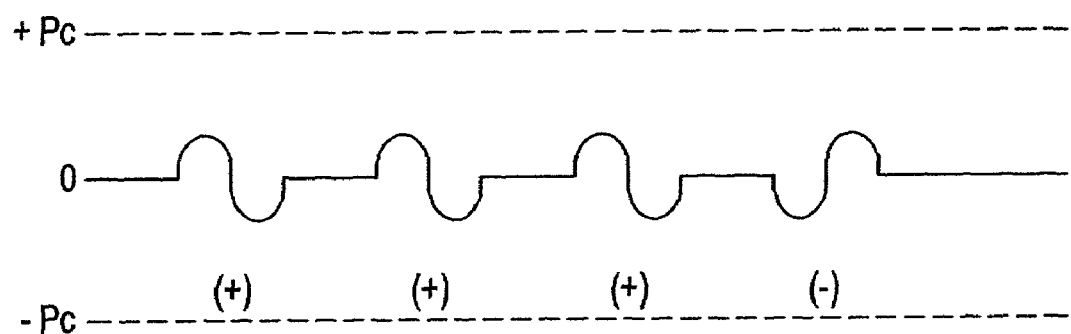
FIGS. 12 and 13 are waveform diagrams of transmitted ultrasound based on an output signal from the modulated signal generating unit.
Figure 13:
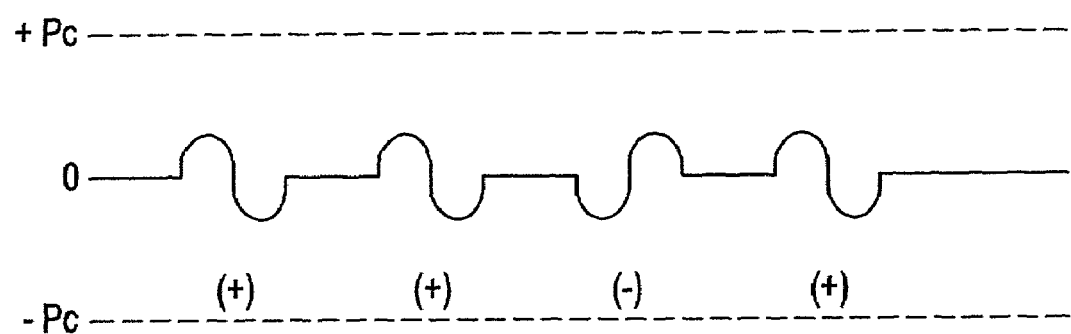

For an echo of the transmitted ultrasound shown in FIG. 12, the autocorrelation calculation is performed using the code sequence [+++−]; and for an echo of the transmitted ultrasound shown in FIG. 13, the autocorrelation calculation is performed using the code sequence [++−+].

Figure 14:
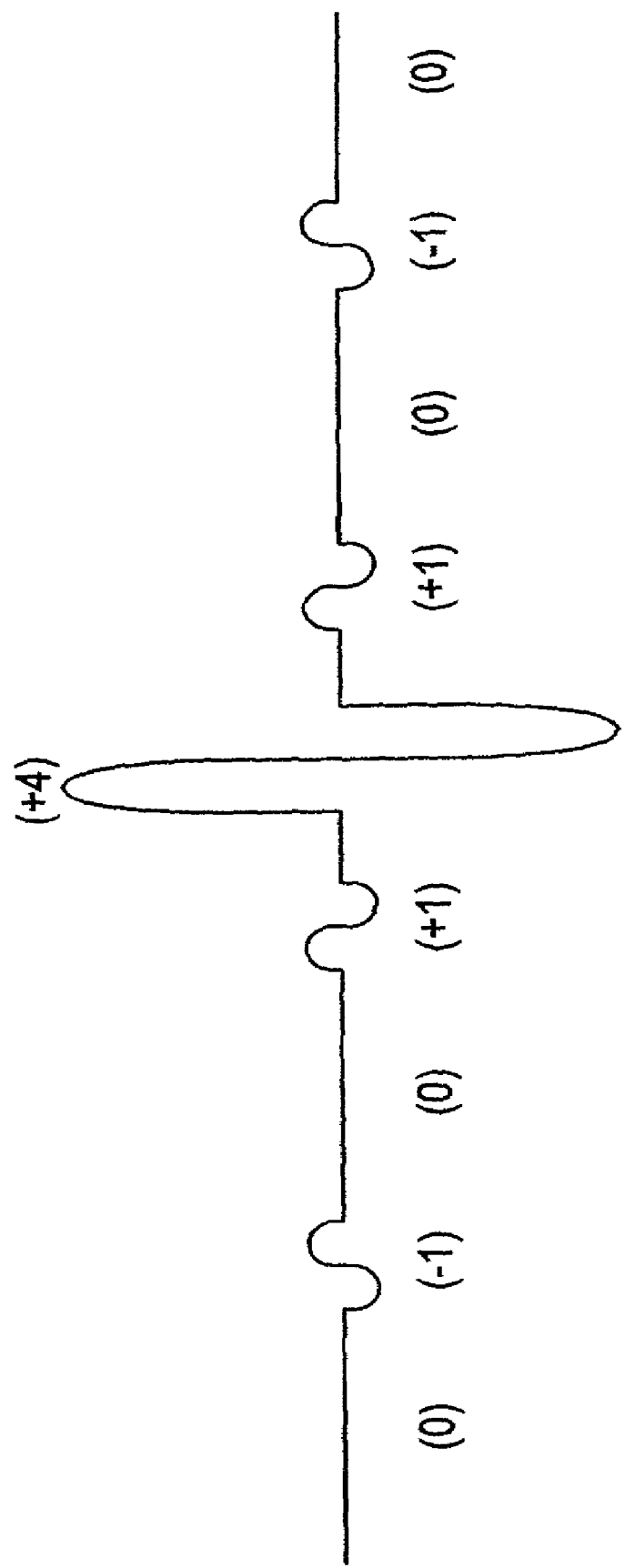
Figure 15:
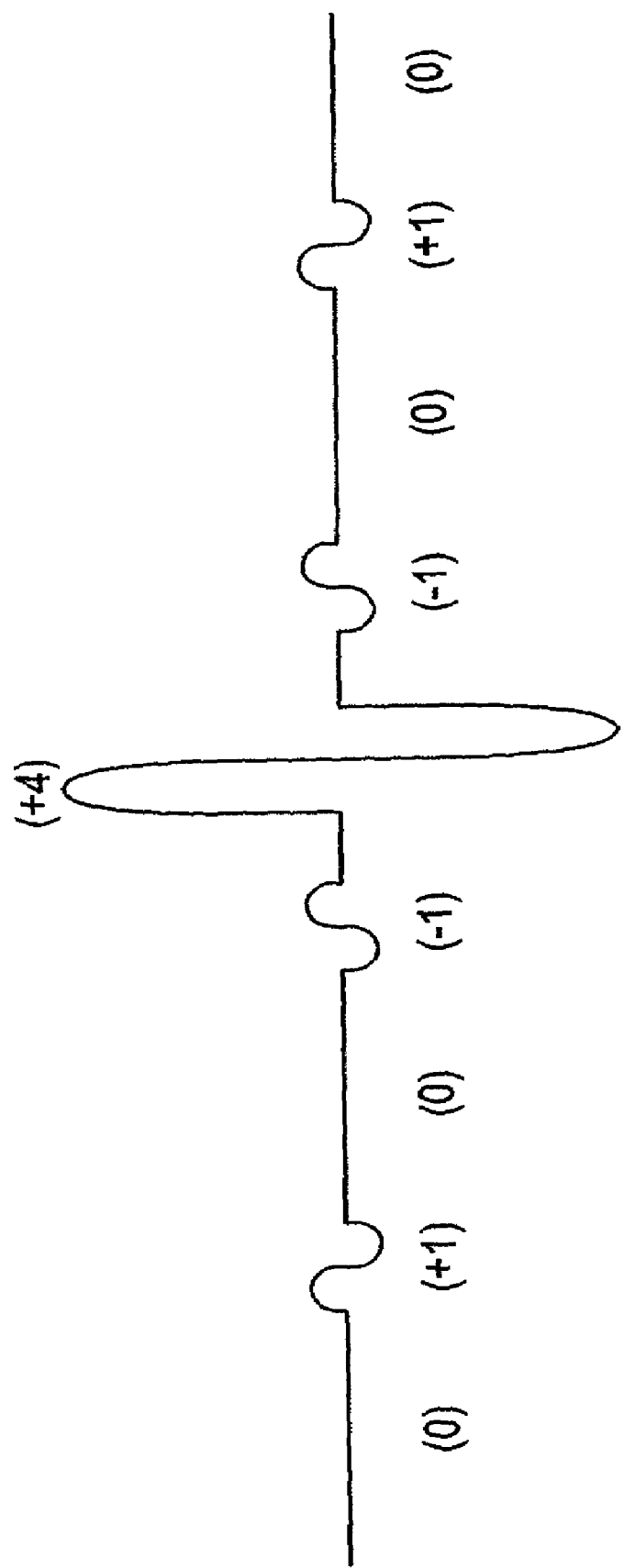
Figure 17A:
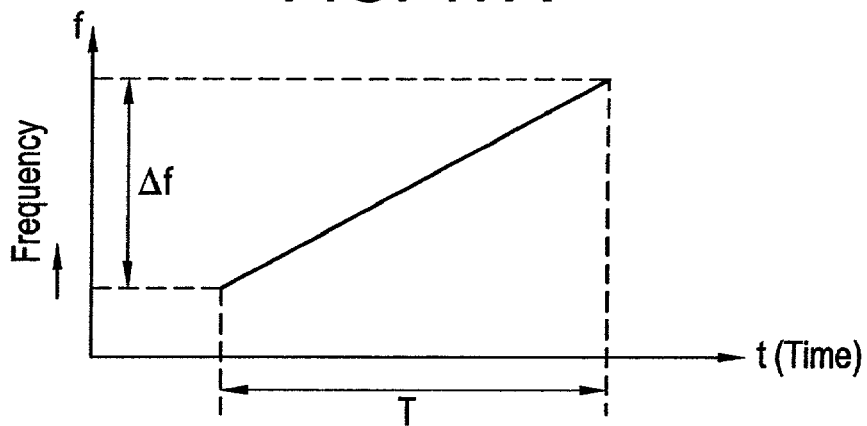
FIG. 17 illustrates linear frequency modulation and corresponding pulse compression.
Figure 17B:
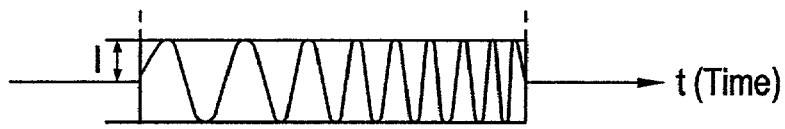
Figure 17C:
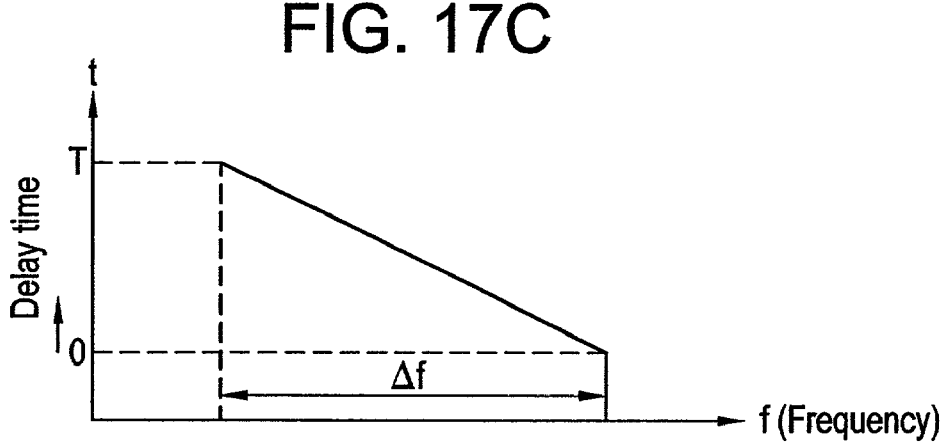
Figure 17D:
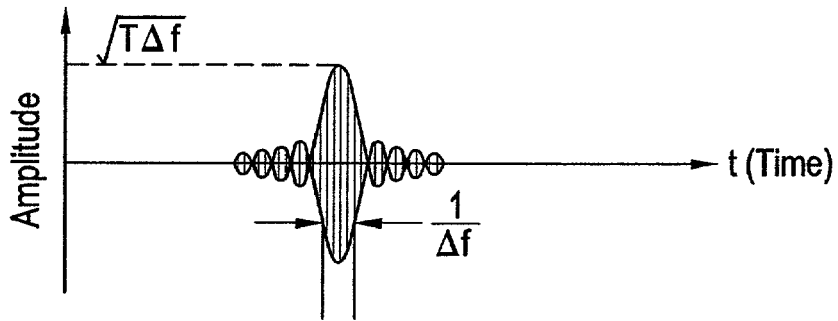

Thus, respective compressed pulses are obtained as shown in FIGS. 14 and 15. The compressed pulse shown in FIG. 14 has a relative amplitude of 0, −1, 0, +1, +4, +1, 0, −1, 0; and the compressed pulse shown in FIG. 15 has a relative amplitude of 0, +1, 0, −1, +4, −1, 0, +1, 0.

By calculating the sum of such compressed pulses, a compressed pulse can be obtained having a center signal of +8 and all the other signals of 0, as shown in FIG. 16. In other words, a pulse that has an even better SNR than by the Barker code can be obtained. Moreover, such a pulse is advantageous in that it has no side lobe because all the signals other than the center signal become zero.

When the Golay code is employed, ultrasound transmission/reception is performed twice for every acoustic line. The first ultrasound transmission/reception is performed using one of the pair of the code sequences, and the second ultrasound transmission/reception is performed using the other. Then, the sum of the first pulse-compressed echo received signal and the second pulse-compressed echo received signal is calculated, and the sum is defined as the echo received signal for one acoustic line. Such transmission/reception is performed while sequentially changing the acoustic line direction.

In lieu of the code modulation, linear frequency modulation may be employed. FIG. 17 shows the concept of the linear frequency modulation and corresponding pulse compression. As shown in FIG. 17($a$), a frequency modulated signal as shown in FIG. 17($b$) having a frequency that linearly changes by f in a time period T is generated by the modulated signal generating unit 624, and ultrasound based on the signal as shown in FIG. 17($b$) is transmitted. Naturally, the sound pressure of the transmitted ultrasound should not be greater than the contrast agent breaking sound pressure Pc.

By performing the pulse compression on an echo received signal of such ultrasound by the pulse compressing unit 614 having a frequency-delay time characteristic such that the delay time varies from T to 0 in the frequency range Δf, as shown in FIG. 17($c$), a compressed pulse having an increased relative amplitude at the signal center can be obtained, as shown in FIG. 17($d$).

A portion including the pulse signal generating unit 622, selecting unit 626, transmission beamformer 604, transmission/reception switching unit 606, ultrasonic probe 2 and reception beamformer 608 is an embodiment of the first ultrasound transmitting/receiving means of the present invention.

A portion including the modulated signal generating unit 624, selecting unit 626, transmission beamformer 604, transmission/reception switching unit 606, ultrasonic probe 2 and reception beamformer 608 is an embodiment of the second ultrasound transmitting/receiving means of the present invention. The pulse compressing unit 614 is an embodiment of the pulse compressing means of the present invention. The control section 18, which will be described later, is an embodiment of the control means of the present invention.

The transceiver section 6 as described above is connected to a B-mode processing section 10 and a Doppler processing section 12, as shown in FIG. 1. The echo received signal for each acoustic line output from the transceiver section 6 is input to the B-mode processing section 10 and the Doppler processing section 12.

The B-mode processing section 10 is for generating B-mode image data. The B-mode processing section 10 logarithmically amplifies the echo received signal and then detects its envelope to obtain a signal indicating the intensity of the echo at each reflection point on an acoustic line, i.e., an A-scope signal; and generates B-mode image data using the amplitude of the A-scope signal at each instant as the brightness. Image data for the aforementioned two kinds of transmitted ultrasound are individually generated as the B-mode image data.

The Doppler processing section 12 is for generating Doppler image data. Image data for the aforementioned two kinds of transmitted ultrasound are individually generated as the Doppler image data. The Doppler processing section 12 quadrature-detects the echo received signal and then MTI (moving target indication)-processes the signal to obtain the Doppler shift in the echo signal; and calculates the average flow velocity, variance of the flow velocity, power of the Doppler signal, etc. from an autocorrelation calculation on the Doppler shift. The average flow velocity will sometimes be referred to simply as the flow velocity hereinbelow. Moreover, the variance of the flow velocity will sometimes be referred to simply as the variance, and the power of the Doppler signal simply as the power hereinbelow.

The Doppler processing section 12 provides data representing the flow velocity, variance and power of an echo source moving inside the object 4 for each acoustic line. The data represents the flow velocity, variance and power at each point (pixel) on an acoustic line. The flow velocity is obtained as a component in an acoustic line direction, and a direction approaching the ultrasonic probe 2 and a direction going away from the ultrasonic probe 2 are distinguished.

The B-mode processing section 10 and the Doppler processing section 12 are connected to an image processing section 14. The image processing section 14 produces a B-mode image and a color Doppler image based on respective data supplied from the B-mode processing section 10 and the Doppler processing section 12. The B-mode image and the color Doppler image are generated for each of the two kinds of transmitted ultrasound.

The image processing section 14 is connected with a display section 16, which displays the B-mode and color Doppler images produced by the image processing section 14. A portion including the B-mode processing section 10, Doppler processing section 12, image processing section 14 and display section 16 is an embodiment of the image producing means of the present invention.

The transceiver section 6, B-mode processing section 10, Doppler processing section 12, image processing section 14 and display section 16 are connected with the control section 18. The control section 18 supplies control signals to these sections for controlling their operation. The control section 18 is supplied with several kinds of notification signals from the controlled sections. The B-mode operation and the Doppler mode operation are executed under the control of the control section 18.

The control section 18 is connected with an operating section 20. The operating section 20 is operated by the user, and the section 20 inputs appropriate instructions and information to the control section 18. The operating section 20 includes, for example, a keyboard, pointing device and other operating devices.

Now the operation of the present apparatus will be described. The user abuts the ultrasonic probe 2 against a desired portion on the object 4, and operates the operating section 20 for performing, for example, B-mode imaging. The imaging is performed under the control of the control section 18.

Figure 3:
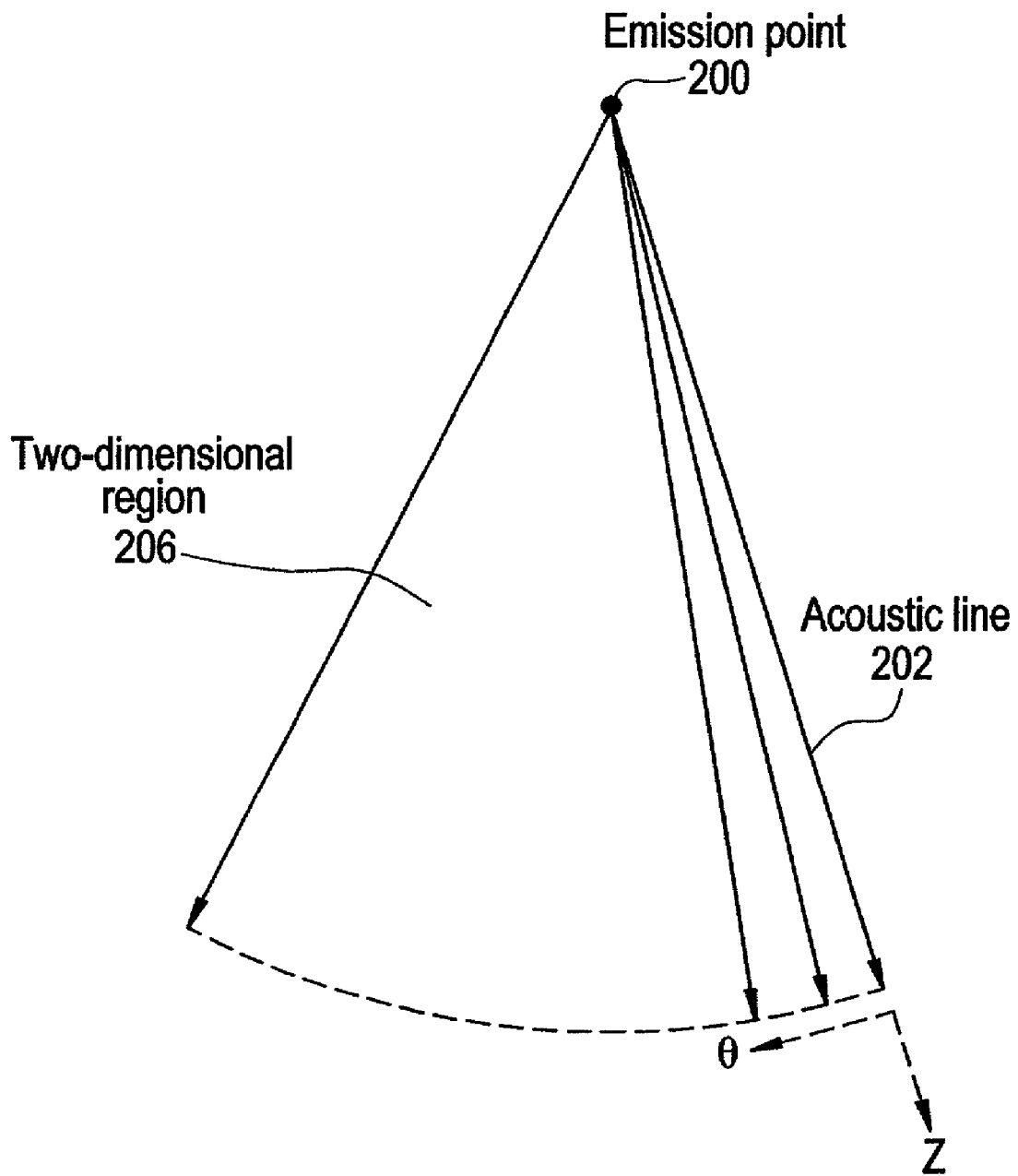
FIGS. 3–5 are schematic diagrams of acoustic line scanning.

The transceiver section 6 performs scanning as shown in FIGS. 3–5 on the interior of the object 4 in an acoustic-line-sequential manner using the ultrasonic probe 2. Of the aforementioned two kinds of transmitted ultrasound, scanning by the ultrasound having a sound pressure greater than the contrast agent breaking sound pressure is intermittently performed with a pause period of from several seconds to several tens of seconds, and scanning by the ultrasound having a sound pressure not greater than the contrast agent breaking sound pressure is continuously performed during the pause period of the intermittent scanning.

Thus, two B-mode images are captured. One of the two B-mode images will be sometimes referred to as a high sound pressure image and the other as a low sound pressure image hereinbelow. These images are displayed next to each other on the screen of the display section 16, as exemplarily shown in FIG. 18.

The high sound pressure image 162 is a contrast image. This image is displayed as a freeze image, and is updated every time a new image is obtained by the intermittent scanning. The low sound pressure image 164 is displayed as a real-time image because it is obtained by the continuous scanning. This image shows the state in real time from the time the contrast agent is broken and to the time it again infuses the site being imaged. Since the image is produced based on the pulse-compressed echo received signal having a high SNR, the image quality is high even if the transmitted ultrasound has a low sound pressure.

While the present invention has been described with reference to preferred embodiments hereinabove, various changes or substitutions may be made on these embodiments by those ordinarily skilled in the art pertinent to the present invention without departing from the technical scope of the present invention. Therefore, the technical scope of the present invention encompasses not only those embodiments described above but all the embodiments that fall within the scope of the appended claims.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic transmission/reception method, comprising the steps of: intermittently scanning an imaged region with a predetermined pause period using a first ultrasound signal that has a sound pressure sufficient to break a contrast agent, and receiving an echo of the first ultrasound signal; continuously scanning the same region as said imaged region during said pause period using a second ultrasound signal that has a sound pressure insufficient to break the contrast agent and has undergone predetermined modulation, and receiving an echo of the second ultrasound signal; and performing pulse compression on an echo received signal obtained by said continuous scanning.

2. The ultrasonic transmission/reception method as defined by claim 1, wherein said modulation is code modulation.

3. The ultrasonic transmission/reception method as defined by claim 2, wherein a code sequence for said code modulation is a Barker code.

4. The ultrasonic transmission/reception method as defined by claim 2, wherein a code sequence for said code modulation is a Golay code.

5. An ultrasonic transmission/reception apparatus, comprising: first ultrasound transmitting/receiving means for intermittently scanning an imaged region using a first ultrasound signal that has a sound pressure sufficient to break a contrast agent, and receiving an echo of the first ultrasound signal; second ultrasound transmitting/receiving means for continuously scanning the same region as said imaged region using a second ultrasound signal that has a sound pressure insufficient to break the contrast agent and has undergone predetermined modulation, and receiving an echo of the second ultrasound signal; pulse compression means for performing pulse compression on an echo received signal from said second ultrasound transmitting/receiving means; and control means for causing said first ultrasound transmitting/receiving means to perform the intermittent scanning with a predetermined pause period, and causing said second ultrasound transmitting/receiving means to perform the continuous scanning during said pause period.

6. The ultrasonic transmission/reception apparatus as defined by claim 5, wherein said modulation is code modulation.

7. The ultrasonic transmission/reception apparatus as defined by claim 6, wherein a code sequence for said code modulation is a Barker code.

8. The ultrasonic transmission/reception apparatus as defined by claim 6, wherein a code sequence for said code modulation is a Golay code.

9. An ultrasonic imaging method, comprising the steps of: intermittently scanning an imaged region with a predetermined pause period using a first ultrasound signal that has a sound pressure sufficient to break a contrast agent, and receiving an echo of the first ultrasound signal; continuously scanning the same region as said imaged region during said pause period using a second ultrasound signal that has a sound pressure insufficient to break the contrast agent and has undergone predetermined modulation, and receiving an echo of the second ultrasound signal; performing pulse compression on an echo received signal obtained by said continuous scanning; and producing respective images based on an echo received signal obtained by said intermittent scanning and on an echo received signal after said pulse compression.

10. The ultrasonic imaging method as defined by claim 9, wherein said modulation is code modulation.

11. The ultrasonic imaging method as defined by claim 10, wherein a code sequence for said code modulation is a Barker code.

12. The ultrasonic imaging method as defined by claim 10, wherein a code sequence for said code modulation is a Golay code.

13. An ultrasonic imaging apparatus, comprising: first ultrasound transmitting/receiving means for intermittently scanning an imaged region using a first ultrasound signal that has a sound pressure sufficient to break a contrast agent, and receiving an echo of the first ultrasound signal; second ultrasound transmitting/receiving means for continuously scanning the same region as said imaged region using a second ultrasound signal that has a sound pressure insufficient to break the contrast agent and has undergone predetermined modulation, and receiving an echo of the second ultrasound signal; pulse compression means for performing pulse compression on an echo received signal from said second ultrasound transmitting/receiving means; control means for causing said first ultrasound transmitting/receiving means to perform the intermittent scanning with a predetermined pause period, and causing said second ultrasound transmitting/receiving means to perform the continuous scanning during said pause period; and image producing means for producing respective images based on an echo received signal from said first ultrasound transmitting/receiving means and on an echo received signal after said pulse compression from said second ultrasound transmitting/receiving means.

14. The ultrasonic imaging apparatus as defined by claim 13, wherein said modulation is code modulation.

15. The ultrasonic imaging apparatus as defined by claim 14, wherein a code sequence for said code modulation is a Barker code.

16. The ultrasonic imaging apparatus as defined by claim 14, wherein a code sequence for said code modulation is a Golay code.

* * * * *